United States Patent
Mohajer-Shojaee

(10) Patent No.: US 12,207,843 B2
(45) Date of Patent: Jan. 28, 2025

(54) RESISTANCE-FREE TROCAR ASSEMBLY

(71) Applicant: Reza Mohajer-Shojaee, Encino, CA (US)

(72) Inventor: Reza Mohajer-Shojaee, Encino, CA (US)

( * ) Notice: Subject to any disclaimer, the term of this patent is extended or adjusted under 35 U.S.C. 154(b) by 0 days.

(21) Appl. No.: 18/737,098

(22) Filed: Jun. 7, 2024

(65) Prior Publication Data
US 2024/0407806 A1    Dec. 12, 2024

Related U.S. Application Data

(60) Provisional application No. 63/472,238, filed on Jun. 9, 2023.

(51) Int. Cl.
| | | |
|---|---|---|
| *A61B 17/34* | (2006.01) | |
| *A61B 17/32* | (2006.01) | |
| *A61B 90/30* | (2016.01) | |
| *A61B 17/00* | (2006.01) | |
| *A61B 17/3211* | (2006.01) | |
| *A61M 25/00* | (2006.01) | |

(52) U.S. Cl.
CPC .. *A61B 17/3496* (2013.01); *A61B 17/320016* (2013.01); *A61B 17/3423* (2013.01); *A61B 17/3462* (2013.01); *A61B 17/3474* (2013.01); *A61B 90/30* (2016.02); *A61B 2017/00734* (2013.01); *A61B 2017/32113* (2013.01); *A61B 2017/3454* (2013.01); *A61B 2090/309* (2016.02); *A61M 25/0082* (2013.01)

(58) Field of Classification Search
CPC . A61B 17/3496; A61B 90/30; A61B 17/3421; A61B 17/3423
See application file for complete search history.

(56) References Cited

U.S. PATENT DOCUMENTS

| | | |
|---|---|---|
| 4,601,710 A | 7/1986 | Moll |
| 5,947,930 A | 9/1999 | Schwemberger et al. |
| 2006/0200182 A1 | 9/2006 | Prosek |
| 2018/0021057 A1* | 1/2018 | Mohajer-Shojaee ......... A61B 17/3496 604/164.12 |
| 2019/0290326 A1 | 9/2019 | Zhu |

OTHER PUBLICATIONS

International Search Report with written opinion issued by the International Searching Authority for International Patent Application No. PCT/US2024/032970, mailed on Sep. 9, 2024.

* cited by examiner

*Primary Examiner* — Si Ming Ku
(74) *Attorney, Agent, or Firm* — Myers Wolin, LLC

(57) ABSTRACT

A trocar assembly includes a head; an elongated tubular structure, having an open proximal end and an open distal end; a stationary cutting component, incorporating a large cutter having two sharp side-blades and a centrally disposed non-cutting soft tip that extends through the open distal end of the tubular structure; and a protection assembly, actuated via a compression spring, comprising a moveable cutter safety casing that extends through the open distal end of the tubular structure to cover the stationary cutting component and retracts from the open distal end to reveal the stationary cutting component. As proximally exerted pressure is applied to the cutter safety casing, a large incision is made in the fascia and the abdominal wall is penetrated, whereby the counter-pressure from the abdominal wall is released and a body cavity is reached safely.

15 Claims, 4 Drawing Sheets

RESISTANCE-FREE TROCAR ASSEMBLY

CROSS REFERENCE TO RELATED APPLICATIONS

This application claims the benefit of U.S. Provisional Patent Application No. 63/472,238 filed on Jun. 9, 2023. The disclosure of U.S. Provisional Patent Application No. 63/472,238 is hereby incorporated by reference.

TECHNICAL FIELD

The present disclosure generally relates to surgical instruments and specifically to a trocar assembly as a surgical instrument and its methods of use for the penetration of a body tissue to establish a conduit for the insertion of other medical instruments.

BACKGROUND

Performing laparoscopic procedures (minimally invasive surgery) in different regimens of medicine are becoming more prevalent and popular as a surgical method. Laparoscopy provides many advantages over the traditional method of laparotomy (open surgery). It is comparatively more precise and less prone to tissue damage and scarring. It produces a shorter hospital stay and less post-operative pain and discomfort, requiring less medication to mitigate pain. It is less traumatic to the patient and more cost-effective for the patient and the insurance companies.

Trocars and Veress needles are used in minimally invasive surgical procedures to establish a pathway or a conduit into the patient's abdominal wall to access an abdominal cavity. During the deployment of the trocar to cut through the patient's abdominal wall, a trocar is mated with a cannula to establish an access port to the abdominal cavity, after which the trocar is removed and the cannula is left therein for the insertion of other medically required instruments, such as endoscopes, cameras, fiber-optic lights, needle drivers for suturing, laparoscopes, bowel grasper, and surgical mesh.

However, use of conventional trocars, such as "Shielded Trocars," has created 75,000 complications annually in the US alone, involving trocar-related injuries to the internal organs, some causing fatality. Consequently, a safer alternative to the current trocar assemblies and methods of use for establishing a conduit to the patient's abdominal cavity is needed.

As an example, when a trocar is used to enter the body cavity in order to establish a port via insertion of a cannula, the currently available dysfunctional "safety shields" of the "Shielded Trocars" are unable to fully safeguard the vital organs from being injured by the cutter. This is because the "safety shields" are large and cannot enter the small opening produced by a small cutter, and are, thus, unable to cover the cutter's sharp tip upon entry into the abdominal cavity.

The applied force at the proximal end of any trocar that is countered by the resistance of the fascia, or any other body tissue, is a major cause of the "overshooting" incidents, resulting in these complications. Currently, the operator increases the proximal force; thus, creating the "overshooting" incidents leading to complications reported in literature. To counter the fascia's resistance to the proximally applied force, a larger incision must be made in the fascia to reduce its resistance, resulting in a smooth and safe penetration of the abdominal wall.

According to the law of physics, smaller tip cutters will make smaller cuts on the fascia. Thereby, by the same law, a protection mechanism, with a larger diameter, will remain stuck above the fascia until there is more pressure exerted at the proximal end of the trocar. In conformity with this law, therefore, almost every "Shielded Trocar" can allow its cutter to enter the body cavity first unprotected. However, it should be noted that, fortunately, this has not resulted in a complete (100%) failure of these trocars. Although, it should also be noted that the resulting 75,000 annual complications in the US alone is jeopardizing the health and the lives of patients and that the design of the "Shielded Trocar" is the major cause of these dangerous complications as its non-functional "safety shield" does not provide protection to the vital organs by allowing the cutter to penetrate the fascia first without the "safety shield." For example, some trocars provide a special tip to cut the fascia claiming to produce a better or an easier cut. In practice, they have been proven to fail in resulting in a safe "entry," as expected. In fact, "overshooting" is a defect of all trocars that do not possess cutters or protection mechanisms similar to the ones being disclosed herein.

The present disclosure suggests that the reason for the prevention of the downright "Shielded Trocar" failure is the air ($CO_2$ gas) that rushes into the body cavity to give a protective layer of air cushion in-between the sharp cutter and the vital organs.

The following references attest to the serious defects of the Shielded Trocars and those with small cutters. Numerous medical literatures analyzing safety of trocars of various structures, especially the Shielded Trocars, affirm the dangers and the inadequacy of existing trocars. These analyses assert that although Shielded Trocars may have been used in an effort to decrease entry injuries, there is "no evidence that they result in fewer visceral and vascular injuries during laparoscopic access."

(1) Dr. Charles E. Miller in a Master Class article entitled "Safe Abdominal Laparoscopic Entry," *Ob.Gyn. News*, Volume. 57, No. 3, April 2022, provides a convincing testament that there have been no changes to the design of trocars to make them safer. He cites Dr. Javier F. Magrina declaring that "50% of injuries to the gastrointestinal tract and major blood vessels occur at entry," as well as that in his study of "1.5 gynecologic patients, about 20-25% of the complication were not recognized until the postoperative period." In his important and very recent article, Dr. Miller states that "[U]se of shielded trocars have not been shown to decrease entry injuries; that is, visceral or vascular injuries have not been shown to decrease."

(2) According to a recent article entitled "A Novel Device for Safe Trocar Insertion in Laparoscopic Surgery Based on the Insertion Force Characteristics," published in the *International Journal of Bioscience, Biochemistry and Bioinformatics*, 6 Volume 9, Number 1, January 2019, there are about 75,000 complications arising from trocar insertions in the US yearly.

(3) The FDA report entitled "Laparoscopic Trocar Injuries: A report from a U.S. Food and Drug Administration (FDA) Center for Devices and Radiological Health (CDRH) Systematic Technology Assessment of Medical Products (STAMP) Committee: FDA Safety Communication" attesting to the problems and dangers of Shielded Trocars. The report was last updated in 2014, which indicates that its assessment is still relevant.

(4) According to the FDA, "In 1984, a trocar was introduced with a retractable shield that covers the tip before and after insertion . . . to protect abdominal and pelvic organs from inadvertent puncture. Whether shielded trocars offer protection against injuries is the subject of debate . . . . A 1996 study . . . involving the use of 386,784 trocars found that ten out of the 26 (39%) serious injuries and two out of the seven (29%) deaths involved shielded trocars . . . . In a 1996, based upon a lack of data to support safety claims, FDA asked manufacturers to refrain from using the term 'safety trocar' to refer to shielded trocars."

The FDA states that it " . . . frequently receives reports of broken trocars and trocar components, sometimes associated with patient lacerations and device fragments left in patients." and believes that discussions about the effectiveness of trocars classified as "shields, optics, radially-expanding designs" will continue because their fail-safe features do not provide prevention against trocar related injury" and assesses that among other reasons, "lack of proven-effective fail-safe features . . . may also contribute to morbidity and mortality."

The FDA also suggests that the "design" of the trocar needs to be improved for it to become safe.

(5) The Emergency Care Research Institute (ECRI)—Americas' "most-respected laboratory for testing medical products"—in its report "Trocars: safety and selection, 1998; 27:376-98. [PubMed: 9859030]" states that the shielded trocars were intended to prevent the sharp tip from injuring intra-abdominal contents, but even when a shielded trocar functions properly and is used according to the specifications, there is a brief moment when the sharp trocar tip is exposed and unprotected as it enters the abdominal cavity." The ECRI concludes that "the shield may create a false sense of security and lead to undue reliance upon it."

In view of the above-described deficiencies experienced by the current trocars, there is a long-felt need for an improvement to the design of trocars. It should be noted that across all these years, no inventor or scholar has been able to solve this very serious problem in this sector of medicine, which needs to be remedied urgently to save lives.

SUMMARY

Contrary to the above-described deficiencies experienced by the current trocars, it is hereby disclosed that the herein conceived modifications will not depend on any "hit or miss" artificial protection. The disclosed larger cutter, the respective slits in the distal ends of the trocar, the cutter safety casing, and the cannula will work together cooperatively to provide unquestionable safety. In this, they are supported by the compression spring's automatic retraction function to force the large cutter into its non-cutting original state as soon as it has made a sufficiently large cut in the fascia for the cutter safety casing to retreat, leaving the trocar and the cannula to easily enter the open body cavity safely.

Previous development by the present inventor in various aspects of trocar has been disclosed in U.S. Pat. Nos. 8,523,817, 8,838,206, 9,579,472, and 10,646,250, contents of which are herein incorporated by reference.

Adopting the presently disclosed design modifications to the corresponding distal components of a "Shielded Trocar," or an "Atraumatic Blunt Tip Trocar," or any other trocar will render them safer by drastically reducing the operator's need to exert excessive pressure at the proximal end of the trocar. More importantly, the disclosed modifications will not give the surgeons a false sense of security.

The herein disclosed modifications to enlarge the cutter to produce a larger fascia incision, enabling the redesigned cutter safety casing to enter the abdominal cavity in advance of, or jointly with, the cutter is indeed a novel and an innovative idea. These modifications have the potential to improve the collaborative mechanical functions of the cutters and the protection mechanisms of all existing trocars in order to control the "overshooting" incidents, making trocars safer.

As stated before, the applied force at the proximal end of any trocar that is countered by the resistance of the fascia, or any other body tissue, is a major cause of "overshooting." To counter the fascia's resistance to the proximally applied force, it is crucial for the trocar's cutter to make a larger opening in the resistive body tissues of the abdominal wall, such as the fascia, so that the cutter safety casing is able to enter the body cavity without difficulty and resistance from the tissues involved. This can be achieved by redesigning the distal end of a trocar, its cutter, its cutter safety casing, and its supplementary cannula.

Therefore, the present disclosure relates to the modification of the cutter to encompass a larger size, as well as the modification of the distal end of the trocar, the cutter safety casing, and the distal end of the supplementary cannula so that each include two diametrically opposed lateral slits of 180-degrees of separation. It is further disclosed that the three different sets of slits will provide an unimpeded vertical passageway that is precisely aligned for the cutter to easily and safely traverse the said collaboratively communicating components to make a large cut in the fascia while remaining within the protective guard of the cutter safety casing and then retreating to its non-cutting mode without making any contact with the vital organs.

Additionally, it is herein disclosed that different configurations of the presently conceived embodiments of the cutter safety casing will each incorporate a similarly described diametrically opposed slits.

Thus, the main objective of the said innovative and unique modifications to the trocar's distal end, the stationary cutting component's enlarged cutter, the cutter safety casing, and the cannula's distal end is to substantially reduce the amount of pressure required at the proximal end of the trocar to eliminate the dangerous "overshooting" incidents.

The above objective will be met because the herein disclosed cutter safety casing's lateral slits will accommodate a larger cutter to be housed within it and for the soft tip 138 of the cutter to easily exit from its distal end. And, because the stationary cutting component—which encompasses a large cutter that includes an elongated post (rod) consisting of two sharp cutting blades at its lateral edges and terminating in a soft tip 138—can protrude from the collaboratively aligned lateral slits of the cutter safety casing, the trocar, and the cannula as the said three sets of slits contiguously form a precise and an unimpeded vertical path for the large cutter to cut the fascia and to return to its original non-cutting mode without injuring any organs.

It is proposed that other advantages can be achieved as a result of the herein disclosed inventor's design improvements to the existing trocars. To enable the cannula to access the abdominal cavity as the trocar cuts the fascia and penetrates the surgical site incision, it is a common medical device manufacturing practice to taper the distal end of the cannula. The tapering is necessitated because the existing trocars make a small cut over the fascia. The tapering results in a cannula having a weaker distal end compared to the other parts of its tubular shaft. It has been reported that the distal end of the cannula sometimes chips and pieces drop, as an example, into the abdominal cavity as the cannula is being maneuvered therein carrying other medical instruments during use.

Two features of the present disclosure remedy this shortcoming: namely, the larger cut over the fascia—produced by the larger cutter—is larger than the distal end of the trocar; and the proposed diametrically opposed slits, creating an easily accessible pathway, will preclude the need to taper the cannula's distal end; thus, eliminating the likelihood of the device chipping and breaking during laparoscopy.

An embodiment of the present disclosure provides trocar assembly including: a head disposed at a proximal end of the trocar assembly; a shaft configured to distally extend from the head and including an open distal end, an open proximal end, and a partial partition wall situated between the open distal end and the open proximal end and respectively defining a distal section and a proximal section, the partial partition wall covering a fraction of the cross-section of the shaft, leaving an opening for a lumen extending from the open distal end to the open proximal end; a cutting component including a tang and a knife blade, the tang being fixed to a location on the distal side of the partial partition wall such that the cutting component is stationary with respect to the shaft, and the knife blade having two lateral cutting edges extending through the open distal end of the shaft at a distal end of the trocar assembly; and a retractable protection assembly configured to one of extend and retract states through the open distal end of the shaft, wherein the retractable protection assembly is configured to extend through the open distal end of the shaft to cover the stationary cutting component in a naturally biased position, and the retractable protection assembly is configured to retract from the open distal end of the shaft to expose the stationary cutting component in a compressed position during application of pressure in a proximal direction to and along a longitudinal axis of the retractable protection assembly, and the retractable protection assembly includes a moveable cutter safety casing configured to house the knife blade and to be coupled with the partial partition wall via a biasing element fixedly attached to the partial partition wall, wherein the cutter safety casing includes a central opening at its proximal end and two diametrically opposed lateral slits of 180-degree of separation at its distal end, and the shaft includes two correspondingly aligned slits at its distal end, such that the cutting component, cutter safety casing and the shaft are nested together in the naturally biased position, and that the knife blade can protrude from the aligned slits of the cutter safety casing and the open distal end of the shaft in the compressed position.

DETAILED DESCRIPTION

Figure 1:
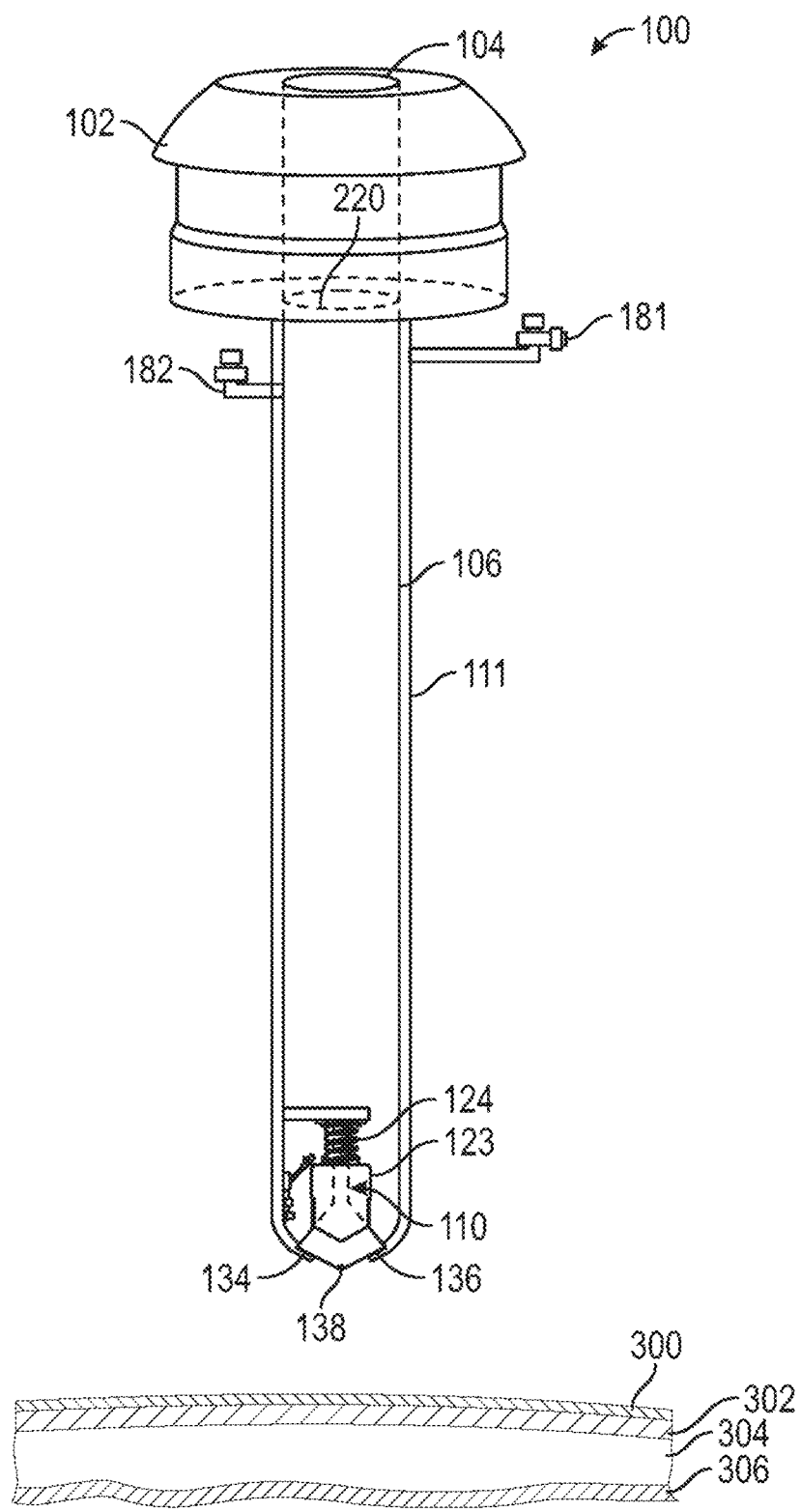
FIG. 1 illustrates a trocar assembly according to an embodiment of the present disclosure.

The description of illustrative embodiments according to principles of the present disclosure is intended to be read in connection with the accompanying drawings, which are to be considered part of the entire written description. In the description of embodiments of the disclosure disclosed herein, any reference to direction or orientation is merely intended for convenience of description and is not intended in any way to limit the scope of the present disclosure. Relative terms such as "lower," "upper," "horizontal," "vertical," "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the disclosure are illustrated by reference to the exemplified embodiments. Accordingly, the disclosure expressly should not be limited to such exemplary embodiments illustrating some possible non-limiting combination of features that may exist alone or in other combinations of features; the scope of the disclosure being defined by the claims appended hereto.

This disclosure describes the best mode or modes of practicing the disclosure as presently contemplated. This description is not intended to be understood in a limiting sense, but provides an example of the disclosure presented solely for illustrative purposes by reference to the accompanying drawings to advise one of ordinary skill in the art of the advantages and construction of the disclosure. In the various views of the drawings, like reference characters designate like or similar parts.

It is important to note that the embodiments disclosed are only examples of the many advantageous uses of the innovative teachings herein. In general, statements made in the specification of the present application do not necessarily limit any of the various claimed disclosures. Moreover, some statements may apply to some inventive features but not to others. In general, unless otherwise indicated, singular elements may be in plural and vice versa with no loss of generality.

As suggested above, the herein described novel and innovative improvements relate to and comply with Sir Isaac Newton's Third Law of Physics that states "for every action (force) in nature there is an equal and opposite reaction: if object A exerts a force on object B, object B also exerts an equal and opposite force on object A."

Accordingly, when pressure is exerted at the proximal end of the trocar to cut the fascia, the same amount of force is received at the distal end of the trocar, generating a counter-pressure from the body tissue. At this time, the operator of the trocar will need to exert more pressure at the proximal end of the trocar to force the cutting blades to cut through the abdominal wall during "first entry," producing an equal counter-force by the distal end to be received by the proximal end. At this juncture, the operator has possibly lost a good portion of control over the device. Because the small cutting blade only makes a small incision in the fascia, the protection mechanism, with its larger diameter, cannot precede the cutting blades into the opening and gets stuck above the fascia, while the cutting blades have already entered the open body cavity, resulting in the occurrence of the globally recognized incidents of the "overshooting" phenomenon.

This is a fact of the law of physics known as "direct response or relationship," where the "variables increase or decrease together."

Thus, the present disclosure concentrates its modifications upon the distal structure of the trocar and its principal components therein, proposing to redesign the cutter to a larger size to produce a larger incision in the fascia; to redesign the cutter safety casing—which protects the sharp cutting blades during penetration—to accommodate the larger cutter and for the cutter safety casing to include a narrower extreme distal end; to redesign the open distal end of the trocar in such a manner to accommodate the larger cutter and the cutter safety casing; and to redesign the open distal end of the trocar's supplementary cannula to accommodate the combined diameters of all of the above named components. These complementary corresponding modifications are intended to result in significant improvements in patient safety by eliminating the resistance of the fascia against the trocar, or by reducing it to a negligible resistance level, at the least.

To use the present disclosed device, the distal end of the trocar assembly is disposed against the skin layer 300 with the underlying fascia transversalis 304 disposed between the muscle 302 and the peritoneum 306 lining the abdominal cavity as shown in FIG. 1.

Including all the embodiments of the presently disclosed resistance-free trocar assembly, the commonly shared components of a trocar are herein briefly disclosed. Referring to FIG. 1, the disclosed trocar assembly 100 includes a horizontally extending cylindrical-shaped head (handle) 102 at its proximal open end 220 and an elongated tubular structure (shaft) 106 at its open distal end 108. The said head is configured to receive pressure during the deployment of the trocar to incise the surgical site. The said head (handle) is further enabled to accommodate placement or attachment of any required auxiliary components of a trocar in general, and of the disclosed trocar in particular. Therefore, the disclosed embodiment further envisions proximally disposed interfaces for the trocar and the cannula. A proximally located cannula interface functions as an insufflation port 181 for delivery of $CO_2$ gas into the body cavity and is provided immediately below the trocar assembly's head (handle). Another proximally disposed trocar interface 182 functions as a port for the trocar in case of using the trocar independently for drainage purposes or in other medical use settings. In one embodiment, the valve 181 is disposed at the proximal end of the cannula shaft to prevent $CO_2$ from escaping. In one embodiment, the port 182 is connected to the proximal end of the trocar, piercing the external wall of the trocar and entering the lumen of the trocar. This port is used for drainage of fluids and gas from the body cavity. The port 182 penetrates the interior of the trocar to connect to the drainage medium.

Figure 2A:
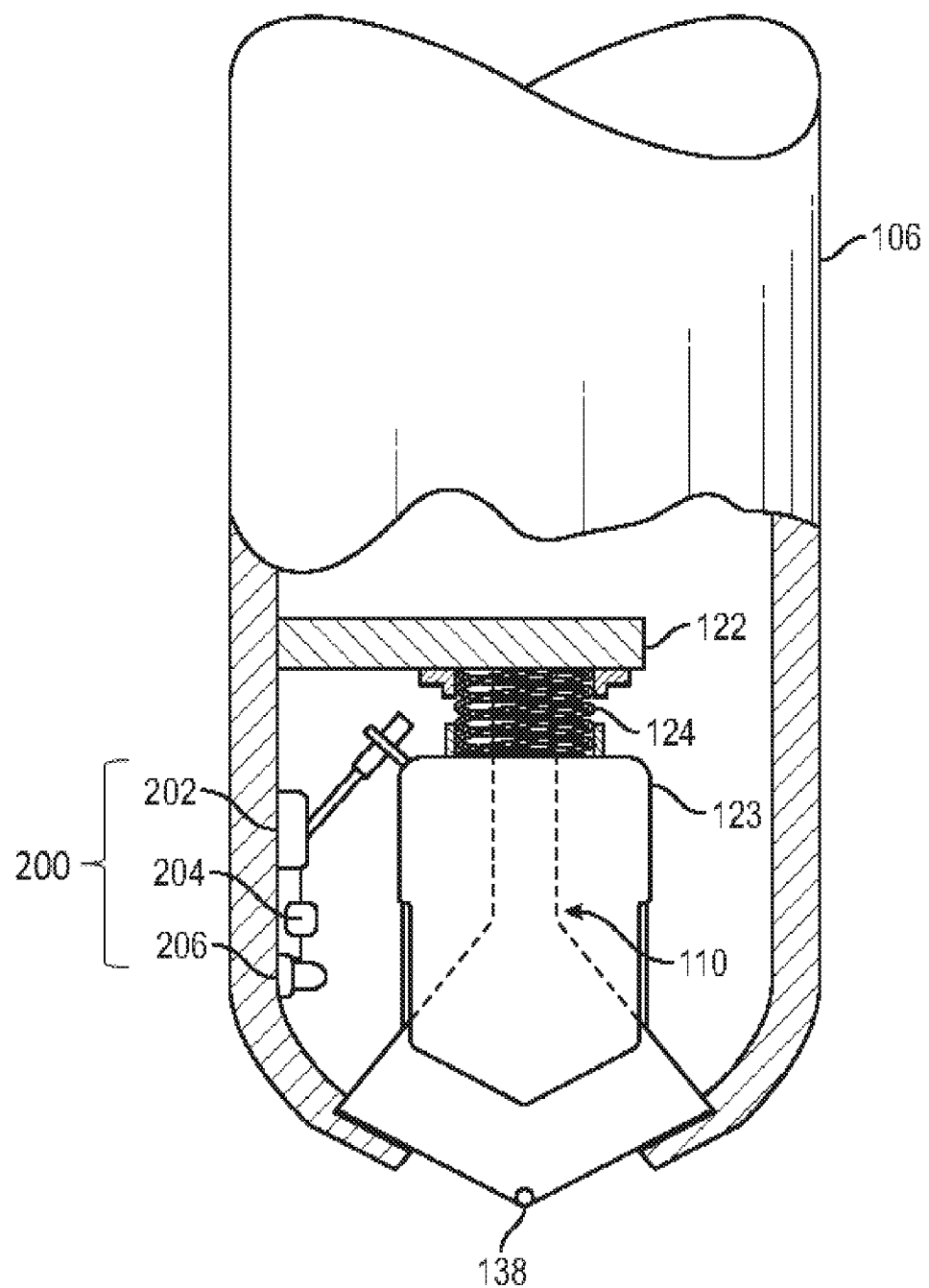
FIG. 2A illustrates a retractable protection assembly in a retract state according to an embodiment of the present disclosure.
Figure 2B:
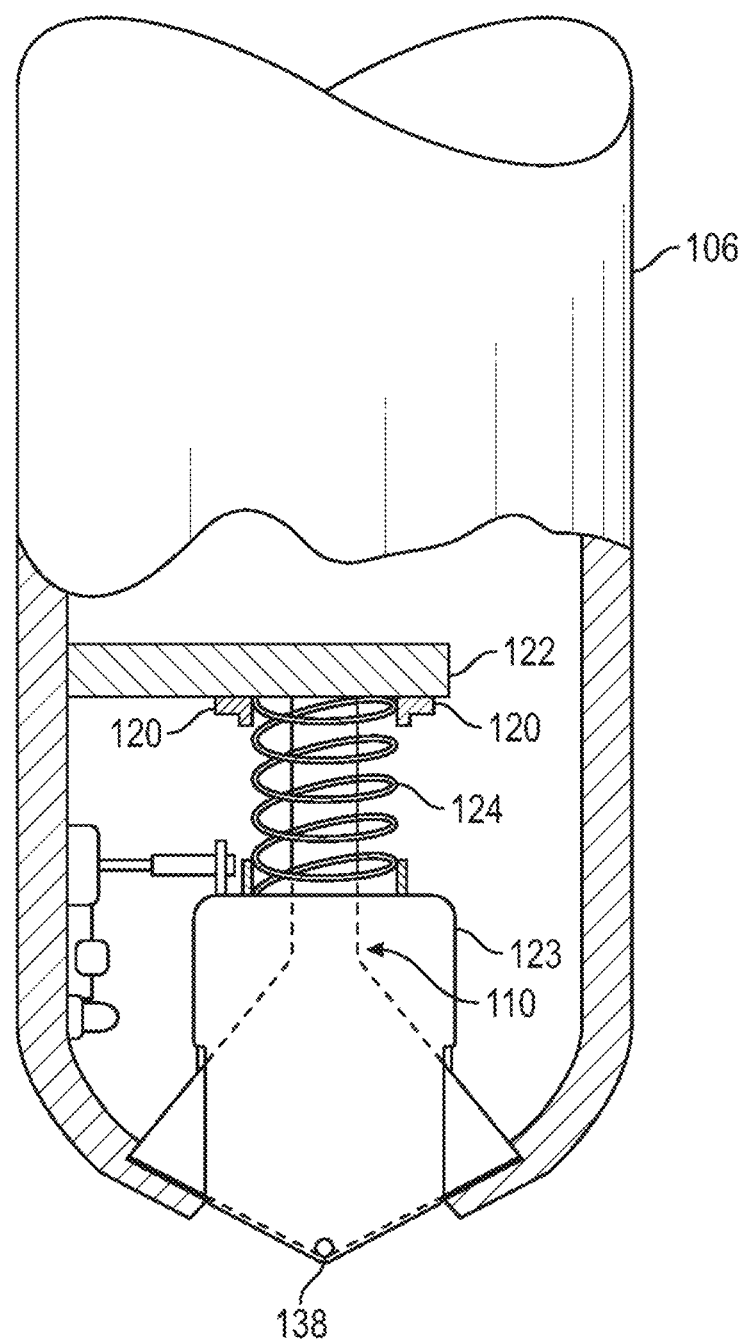
FIG. 2B illustrates a retractable protection assembly in an extend state according to an embodiment of the present disclosure.
Figure 4:
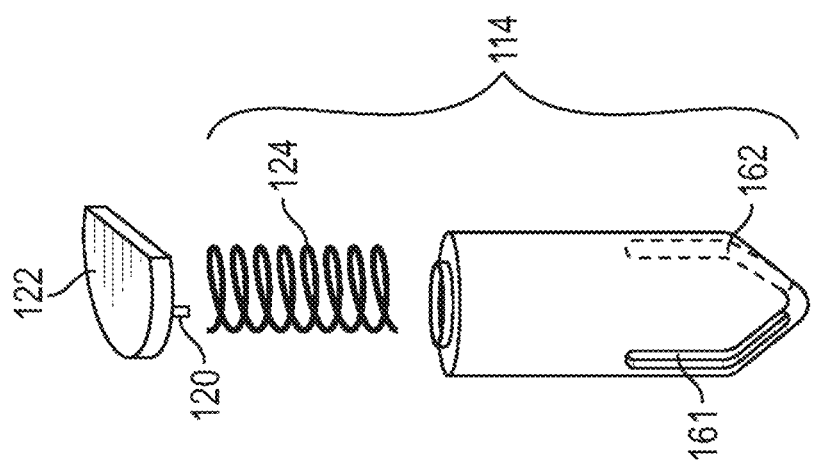
FIG. 4 illustrates a retractable protection assembly according to an embodiment of the present disclosure.
Figure 3:
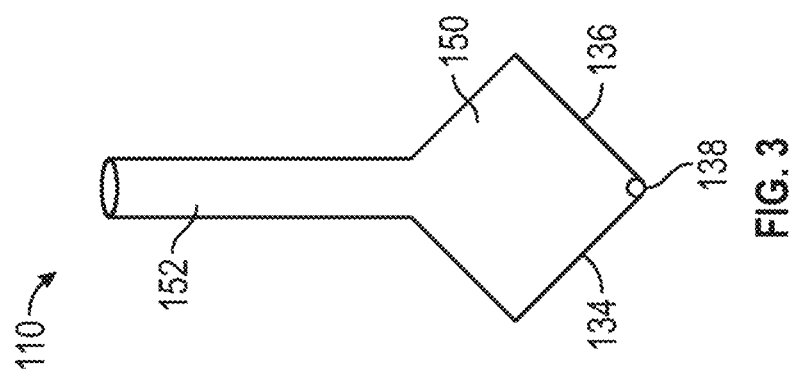
FIG. 3 illustrates a cutting component according to another embodiment of the present disclosure.

Therefore, concentrating on the modification of the main distal components responsible for cutting the fascia safely during the "first entry," it is further disclosed to redesign the trocar assembly's cutting component so that the cutter is made larger and capable of protruding through the lateral slits 161, 162 of the movable cutter safety casing as shown in FIG. 4 to produce the intended larger cut in the fascia. As shown in FIGS. 2A and 2B, the cutter 110 is stationary, residing within the cutter safety casing 123 and dependent upon the movement of the cutter safety casing for changing from a non-cutting mode to a cutting mode and vice versa, as the occasion requires.

The moveable cutter safety casing 123 has a vertical motion which is actuated and controlled by the expanding and the contracting motions of the compression spring 124, whereby it is moved to instantaneously accompany and cover the large cutter as both momentarily enter the body cavity as the larger cutter cuts the fascia. Hence, upon cutting the fascia and entering the body cavity, the large cutter and the cutter safety casing immediately revert to a non-cutting safe mode, retreating to their original states.

It is herein disclosed that the proximal end of the said compression spring 124 is fixed, while the distal end of the compression spring is snugly positioned on the proximal end of the cutter safety casing. In such orientation, the said compression spring cannot move laterally or be dislodged from its position uninvoked. However, the compression spring is inherently configured to vertically expand and retract as induced (prodded).

It is herein disclosed that in one embodiment, the cutting component 110 encompasses a long vertical arm (tang) 152 and a knife blade 150. The long vertical arm (post) of the said stationary cutting component 110 includes a rod that terminates in a large cutter consisting of a soft tip 138 that rests at the extreme distal end of the cutter safety casing 123. The sharp cutting side-blades 134, 136 of the large cutter are composed of a short segment of the cutting component rod, abutting the non-cutting soft tip 138, whereby the said sharp cutting side-blades protrude through the lateral slits of the cutter safety casing 161, 162 in a functional mode.

The integrated disclosed stationary cutting component 110, the compression spring 124, and the cutter safety casing 123 are disposed within the inner shaft of the trocar, whereby the nesting (incorporated) components and the trocar are, in turn, slidably positioned within the inner cavity of the cannula, traversing smoothly without any apparent gaps or friction.

It is further disclosed that the stationary cutting component is anchored to an inner wall of the trocar at the end of the long arm, disposed at an appropriate distance from the distal end of the trocar. In one embodiment, the stationary cutting component is anchored to the partial partition wall, such that the partial partition wall serves two functions, providing an anchor point for the cutting component, and providing a lumen extending from the proximal end to the distal end of the trocar. To provide a larger contact surface between the long arm (tang) of the cutting component and the anchor point of the inner wall, the end of the long arm may have a short horizontal extension in one embodiment, such that the long arm has a reverse L-shaped end. The short horizontal extension provides more contact area when it is fused with the inner wall.

To the long vertical arms (tang) 152 of the stationary cutting component is affixed a compression spring 124, which extends distally through the small and appropriately sized central opening of the proximal end of the cutter safety casing. Therefore, it is further disclosed that the said cutter safety casing has an open proximal end and an open distal end accommodating the long vertical arm (post) of the cutting component to extend through its inner confines and slightly beyond to cut the fascia.

In its initial contact with the fascia, the disclosed larger cutter's most extreme distal portion's soft tip does not cause any harm or damage because the soft tip is unable to cut or penetrate the fascia. But the said soft tip "tents" the fascia upon contact, which immediately gathers the fascia toward the abutting sharp cutting blade edges of the cutter, whereby the "tenting" enables the sharp cutting blade edges to incise a large opening in the fascia, resulting in a "safe entry." A delay in the return of pinched skin to a flat position after it has been tugged, elevated above the rest of the epidermis, and released.

In an embodiment, it is further disclosed that the cutting component encompasses a partial partition wall 122, a structurally thrusted out horizontal planar bar, creating an extension (partial partition wall) that protrudes, to a restrictively limited extent, from an inner wall of the tubular trocar towards its inner cavity. The said planar extension (partial partition wall) defines a partial diameter of the trocar. An opening left by the partial partition allows for a lumen extending from the open distal end to the open proximal end, and the partition further divides the lumen of the trocar into two sections consisting of a proximal end and a distal end. The said planar extension (partial partition wall) 122 is disposed at an appropriate distance from the distal end of the trocar.

The herein disclosed planar extension (partial partition wall) 122 includes a long vertical stabilizing post fixedly attached to the inner wall of the trocar and two shorter vertical posts. One shorter vertically protruding post 120 is oriented distally and is disposed midway along the length of the extension (partial partition wall) 122. The second similarly configured shorter post defines and terminates the horizontal boundary of the said planar extension ((partial partition wall). The defined structure of the planar extension (partial partition wall) can consist of a suitable medical-grade material, such as plastic or metal.

It is herein further disclosed that the said two shorter vertical posts 120 enclose a space that defines the horizontal boundaries of a housing for the compression spring and the large cutter, stabilizing and limiting any side-to-side movements of the said components during deployment. Within the confines of the said housing, formed by the two short vertical posts 120 of the planar extension (partial partition wall), is affixed a compression spring 124, which is snugly positioned on the proximal end of the cutter safety casing, and capable of extending distally through the small and appropriately sized central opening of the proximal end of the cutter safety casing. The said compression spring 124 is inherently configured to vertically expand and retract, as induced (prodded). The large cutter is centrally disposed within the cavity of the compression spring 124. The cutter 110 and the compression spring 124 are affixed at their proximal ends to the distal end of the planar extension (partial partition wall) 122 and project downward towards the distal end of the trocar.

Thus, the larger cutter 110 results in a bigger cut over the fascia, allowing the proposed cutter safety casing to enter the abdominal cavity before the sharp cutting blade edges of the cutter can make contact with any vital organ, such as the bowel, to incur injury. Once the fascia's resistance is removed, the compression spring will automatically retract the cutter into the protective cover of the cutter safety casing.

In effect, the present disclosure is herein proposing the old surgical method of the safe open surgery (laparotomy) in service of minimally invasive surgery (laparoscopy). It is herein proposed that the conceived new structure of the cutter safety casing will cover the sharp cutting blade edges of the cutter for a safer and a more effective operation.

The herein disclosed modification to the safety feature of the trocar conceives a funnel-shaped cutter safety casing in its one embodiment, and a triangular-shaped cutter safety casing in another embodiment, while yet in another embodiment a cutter safety casing can be shaped from two separate pieces—an anterior section and a posterior section.

In the two differently shaped cutter safety casing embodiments herein disclosed—namely, the funnel-shaped cutter safety casing and the triangular-shaped cutter safety casing—the structures will include two lateral slits 161, 162 of similar features disposed at their sides, while the two-piece cutter safety casing embodiment will include two diametrically opposed lateral slits of 180-degrees of separation by default. The diametrically opposed slits of 180-degrees of separation are proposed herein to create an open distal end, where the cutter safety casing is smaller at its most distal end and the lateral sharp outer edges of the cutting blades of the large cutter can protrude externally through the said diametrically opposed slits, forming a pathway for the large cutter and the said cutter safety casing to cooperatively enter the abdominal cavity, with the cutter safety casing entering the body cavity immediately before the large cutter.

The said cutter safety casing extends through the open distal end of the trocar 108, covering the large cutter in a naturally biased position; it retracts from the open distal end, exposing the large cutter in a compressed position during application of body pressure to it until it reaches a body cavity. At reaching the body cavity and eliminating the counter-pressure, the cutter safety casing returns to its naturally biased position.

In one embodiment, a cutter safety casing can be designed and configured from two separate pieces—an anterior section and a posterior section—that can function with one or two springs fixedly attached at the proximal end of each cutter safety casing piece. This embodiment can either have a funnel-shaped or a triangular-shaped cutter safety casing, where the cutter safety casing will be formed from two sections, one piece in front and one piece in the back, which by default will embed two diametrically opposed slits of 180-degrees of separation, as well as having narrower (smaller) extreme distal end diameters.

Figure 5:
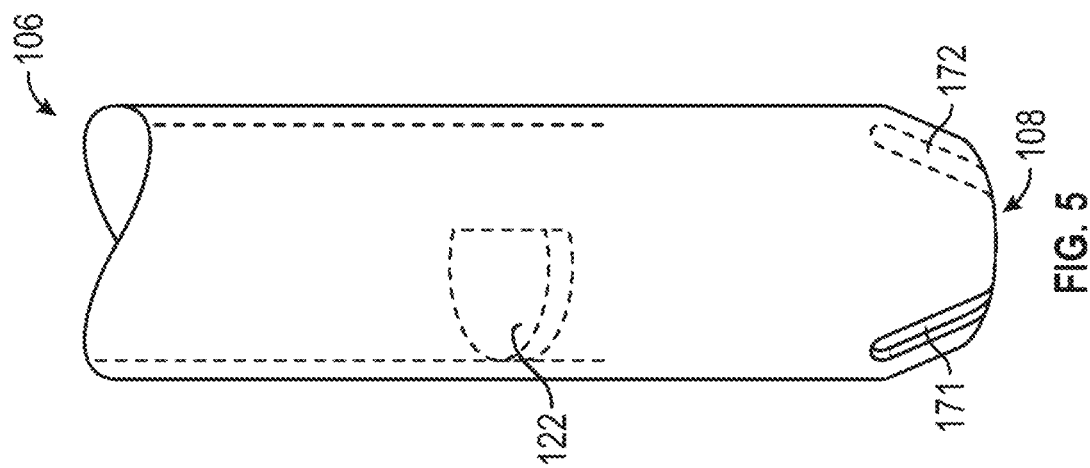
FIG. 5 illustrates a distal portion of a trocar shaft according to an embodiment of the present disclosure.

Additionally, the present disclosure herein discloses that the distal end of the trocar similarly includes two diametrically opposed slits 171, 172 of 180-degrees of separation as shown in FIG. 5 that collaboratively communicate with the said cutter safety casing's side-slits. Thus, the said distally disposed trocar slits 171, 172, in conjunction with the corresponding and parallel slits 161, 162 of the distal end of the cutter safety casing, form a contiguous and precisely aligned unimpeded pathway for the large cutter to extend distally momentarily to cut the fascia.

Thereby it is because of this precisely devised structure that when the trocar is pressed against the patient's targeted body tissue and a minimal amount of pressure is exerted proximally, the compression spring actuates the cutter safety casing to enable it to jointly move with the large cutter, disposed within its interior, downward so that the cutter safety casing and the large cutter can smoothly traverse the sets of the vertically aligned slits to make a large cut across the fascia, allowing the trocar and the cannula to enter the open abdominal cavity without any impediment and without injuring any of the vital organs. When the fascia has safely been incised, the compression spring immediately retracts the cutter safety casing and the enclosed sharp cutting blade edges of the large cutter into the safe non-cutting original position.

The slits at the distal end of the cannula, the trocar, and the cutter safety casing accommodate different sizes of the cutting side-blades.

Thus, the trocar assembly proposed in the present disclosure has a number of unique advantages over existing devices:

- The lateral cuts at the opposing sides of the distal end of the moveable cutter safety casing, which houses the blade, accommodates a larger cutting blade to fit within its inner space (receptacle). The effect of the unique bi-lateral slits is the elimination or the significant reduction of the "overshooting" phenomenon.
- A larger blade reduces the force needed at the proximal end of the trocar to enter the body cavity, which results in the distal end of the trocar not having to hang over the fascia. By making a larger cut on the protective layer of the body cavity, the trauma that can occur to the vital organs can be eliminated or significantly reduced.
- The trocar's cutter safety casing, which houses the cutter, and the cannula shaft each have a set of bi-lateral slits at their distal ends. These precisely designed sets of bi-lateral slits cooperate and communicate with each other to form an unimpeded vertical passageway (conduit) for the large cutter to easily and safely move through the above elements to make a large cut in the fascia. During deployment, the large cutter remains within the protective cover of the cutter safety casing. Having cut the fascia, it then immediately returns to its non-cutting mode without having made any contact with the vital organs.
- The horizontal partial partition wall, separator wall or divider wall occupying part of the trocar's interior cavity. The partial partition wall, separator wall or divider wall can be fixedly placed at the inner wall of the device, leaving an open path from the proximal end to the distal end.
- Thus, the proposed trocar can be a conduit for performing many related tasks and introduction of other devices into the body cavity. The moveable cutter safety casing, with its bi-lateral slits and with a larger blade embedded within it, enters the body cavity without resistance, making a larger opening for insertion of other medical instruments, such as in stent placements and in cardiothoracic and vascular surgeries.
- The vertically open lumen enables the flow of fluids and gas ($CO_2$) through its interior cavity to reach any distally targeted site, where the operator can aspirate or inject medicine or other fluids into the body cavity from the proximal opening.
- Since the mechanical design of the trocar allows the proximal end and the distal end to seamlessly communicate with each other via its unimpeded vertical length of the open lumen, the structure can function as an indicator of where the device is within the body cavity, providing an early warning signal to the operator. For instance, when the device hits an artery, the blood will flow upwards, warning the operator that the distal end of the trocar is in the wrong space and that immediate corrective action is necessary.
- Because the sections of the device are not compartmented into separately inaccessible proximal and distal ends, the partial partition wall, separator wall or divider wall makes it convenient for "non-disposable" devices to be drained of debris and to be cleaned for next use.

In one embodiment, the trocar assembly further includes a switch assembly 200. As shown in FIG. 2A, the switch assembly 200 may include components disposed below or above the partial partition wall 122 that are attached to the inner wall of the shaft 106. The components may include, for example, an automatic switch 202 disposed below the partial partition wall 122, an electronic storage device such as a battery 204, and an illumination device 206. The automatic switch 202, the battery 204, and the illumination device 206 are in electronic communication through one or more wires 208. The illumination device may include at least one light-emitting diode (LED). The battery 204 may be an alkaline coin battery or a battery pack.

The automatic switch 202 may be configured to be in a first position when the retractable protection assembly is in the naturally biased position. Further, automatic switch 202 may be configured to be in a second position when the retractable protection assembly is in the compressed position such that movement of the retractable protection assembly is configured to effect movement of the automatic switch 202. The first position is one of an ON state and an OFF state, and the second position is the other of the ON state and the OFF state. The illumination device 206 is configured to be in an illuminated state when the automatic switch 202 is in the ON state and to be in a non-illuminated state when the automatic switch 202 is in the OFF state. Thus, the LED will turn on (i.e., be in the illuminated state) when the automatic switch 202 is in the ON state and will turn off (i.e., be in the non-illuminated state) when the automatic switch 202 is in the OFF state.

In an embodiment (not shown), the switch assembly may include a manual switch. The manual switch may be disposed on an outer surface of the head of the trocar assembly, which is similar to the trocar assembly 100 of FIG. 1 except for the manual switch and an additional, secondary electronic storage device. The manual switch may be connected to the additional, secondary electronic storage device through one or more wires, such as a wire, that extends through the lumen advancing from the head 102 through an open proximal end of the shaft and through an opening of the shaft 106 defined by the partial partition wall of the shaft.

Thus, the switch assembly of the trocar assembly includes the manual switch, the illumination device, and an electronic storage device including the battery and the secondary electronic storage device. The electronic storage device, including the battery and the secondary electronic storage device, and the illumination device re disposed within the shaft. The battery is disposed distally below the partial partition wall, and the secondary electronic storage device is disposed proximally above the partial partition wall. As a non-limiting example, the secondary electronic storage device includes an alkaline battery pack disposed proximally above the partial partition wall, and the illumination device 206 comprises at least one light-emitting diode (LED) disposed below or above the partial partition wall. The manual switch, the electronic storage device, and the illumination device 206 are in electronic communication through one or more wires.

The manual switch is configured to switch between an ON state and an OFF state through manual compression. The LED is configured to be in an illuminated state when the manual switch is in the ON state and to be in a non-illuminated state when the manual switch is in the OFF state.

While the present disclosure describes at some length and with some particularity with respect to the several described embodiments, it is not intended that it should be limited to any such particulars or embodiments or any particular embodiment, but it is to be construed so as to provide the broadest possible interpretation in view of the related art and, therefore, to effectively encompass various embodiments herein. Furthermore, the foregoing describes various embodiments foreseen by the inventor for which an enabling description was available, notwithstanding those modifications of the disclosure, not presently foreseen, may nonetheless represent equivalents thereto.

The invention claimed is:

1. A trocar assembly (100) comprising:
a head (102) disposed at a proximal end (104) of the trocar assembly (100);
a shaft (106) configured to distally extend from the head (102) and comprising an open distal end (108), an open proximal end (220), and a partial partition wall (122) situated between the open distal end (108) and the open proximal end (220) and respectively defining a distal section and a proximal section, the partial partition wall (122) covering a fraction of the cross-section of the shaft and leaving an opening for a lumen extending from the open distal end (108) to the open proximal end (220);
a cutting component (110) comprising a tang (152) and a knife blade (150), the tang being fixed to a location on a distal side of the partial partition wall such that the cutting component is stationary with respect to the shaft, and the knife blade having two lateral cutting edges (134, 136) extending through the open distal end of the shaft at a distal end of the trocar assembly; and
a retractable protection assembly (114) configured to one of extend and retract states through the open distal end of the shaft, wherein the retractable protection assembly is configured to extend through the open distal end of the shaft (108) to cover the stationary cutting component (110) in a naturally biased position, and the retractable protection assembly is configured to retract from the open distal end of the shaft to expose the stationary cutting component in a compressed position during application of pressure in a proximal direction to and along a longitudinal axis of the retractable protection assembly, and the retractable protection assembly comprises a cutter safety casing (123) configured to house the knife blade (150) and to be coupled with the partial partition wall (122) via a biasing element (124), wherein the cutter safety casing (123) comprises a central opening at its proximal end for the tang to pass through and two diametrically opposed lateral slits (161, 162) of 180-degree of separation at its distal end, and the shaft comprises two correspondingly aligned slits (171, 172) at its distal end, such that the cutting component, cutter safety casing and the shaft are nested together in the naturally biased position, and that the knife blade can protrude from the aligned slits of the cutter safety casing and the open distal end of the shaft in the compressed position.

2. The trocar assembly of claim 1, wherein the biasing element is a coil spring configured to be disposed around the tang of the cutting component, one end of the coil spring is connected to the cutter safety casing and the other end of the coil spring is connected to the distal side of the partial partition wall, the distal side of the partial partition wall comprises a plurality of posts configured to restrict a lateral movement of the coil spring, and when the coil spring is in the naturally biased position, the cutter safety casing and the open distal end of the shaft are configured to house the knife blade.

3. The trocar assembly of claim 1, wherein the two cutting edges of the knife blade terminate in a non-cutting soft tip (138) which rests at an extreme distal end of the cutter safety casing when the retractable protection assembly is in the naturally biased position.

4. The trocar assembly of claim 1, wherein the distal end of the cutter safety casing is of funnel shape or triangular shape.

5. The trocar assembly of claim 1, wherein the cutter safety casing comprises a front piece and a back piece, and the front and back pieces are shaped such that when the front and back pieces are put together, the two diametrically opposed lateral slits of 180-degree of separation are formed.

6. The trocar assembly of claim 1, further comprising a valve (181) to prevent $CO_2$ from escaping the assembly, and an insufflation port (182) for drainage.

7. The trocar assembly of claim 1, further comprising a switch assembly (200).

8. The trocar assembly of claim 7, wherein the switch assembly (200) is disposed distally below the partial partition wall and the switch assembly comprises an automatic switch (202), an electronic storage device (204), and an illumination device (206), and the automatic switch, the electronic storage device, and the illumination device are in electronic communication through one or more wires.

9. The trocar assembly of claim 8, wherein the automatic switch is configured to be in a first position when the retractable protection assembly is in the naturally biased position and to be in a second position when the retractable protection assembly is in the compressed position such that movement of the retractable protection assembly is configured to effect movement of the automatic switch.

10. The trocar assembly of claim 8, wherein the electronic storage device comprises a battery and the illumination device comprises at least one light-emitting diode (LED) disposed below or above the partial partition wall.

11. The trocar assembly of claim 7, wherein the switch assembly comprises a manual switch disposed on an outer surface of the head of the trocar assembly, an electronic storage device, and an illumination device, the electronic storage device and the illumination device disposed within the shaft, and the manual switch, the electronic storage device, and the illumination device are in electronic communication through one or more wires.

12. The trocar assembly of claim 11, wherein the electronic storage device comprises a battery and a secondary electronic storage device, and the battery disposed below or above the partial partition wall.

13. The trocar assembly of claim 12, wherein the secondary electronic storage device comprises an alkaline battery pack disposed above the divider wall, and the illumination device comprises at least one light-emitting diode (LED) disposed below or above the partial partition wall.

14. The trocar assembly of claim 13, wherein the proximally disposed manual switch is configured to switch between an ON state and an OFF state through manual compression, and the LED is configured to be in an illuminated state when the manual switch is in the ON state and to be in a non-illuminated state when the manual switch is in the OFF state.

15. The trocar assembly of claim 7, wherein:
the switch assembly further comprises an automatic switch disposed below the partial partition wall, and movement of the retractable protection assembly is configured to effect movement of the automatic switch such that the LED is configured to be in an illuminated state when the automatic switch is in an ON state, and the LED is configured to be in a non-illuminated state when the automatic switch is in an OFF state.

* * * * *